(12) United States Patent
Grosch et al.

(10) Patent No.: US 6,844,467 B2
(45) Date of Patent: Jan. 18, 2005

(54) METHOD FOR THE PRODUCTION OF GLYCERIC ACID

(75) Inventors: Georg Heinrich Grosch, Bad Duerkheim (DE); Werner Bochnitschek, Ludwigshafen (DE); Peter Neumann, Mannheim (DE); Arend Jouke Kingma, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/469,929

(22) PCT Filed: Mar. 5, 2002

(86) PCT No.: PCT/EP02/02406

§ 371 (c)(1),
(2), (4) Date: Sep. 5, 2003

(87) PCT Pub. No.: WO02/070450

PCT Pub. Date: Sep. 12, 2002

(65) Prior Publication Data

US 2004/0097753 A1 May 20, 2004

(30) Foreign Application Priority Data

Mar. 7, 2001 (DE) .......... 101 10 849

(51) Int. Cl.⁷ .......... C07C 59/10; C07C 59/48
(52) U.S. Cl. .......... 562/587; 562/470
(58) Field of Search .......... 562/587, 470

(56) References Cited

U.S. PATENT DOCUMENTS 3,846,478 A    11/1974   Cummins

FOREIGN PATENT DOCUMENTS

| DE | 37 12 330 | 10/1988 |
| DE | 38 29 829 | 3/1990 |
| DE | 42 28 487 | 3/1993 |
| GB | 1 286 894 | 8/1972 |
| JP | 60-226842 | 11/1985 |
| JP | 10 127299 | 5/1998 |

OTHER PUBLICATIONS

S. Sugiyama et al.: "Selective preparation of 2,3–epoxypropanamide and its facile conversion to 2,3–dihydroxypropanamide with acidic resins" Bulletin of the Chemical Society of Japan, vol. 62, No. 10, pp. 3202–3206, 1989.

J. English et al.: "The dehydration of some alpha,beta–dihydroxy esters" Journal of the Americal Chemical Society, vol. 77, pp. 4661–4664 1955.

Database Crossfire Beilstein 'Online! Beilstein Institut zur Foerderung der Chemischen Wissenschaften, Frankfurt am Main, DE Database accession No. 356606, XP002206284.

Database Crossfire Beilstein 'Online! Beilstein Institut zur Foerderung der Chemischen Wissenschaften, Frankfurt am Main, DE Database accession No. 329484, XP002206285.

Database Crossfire Beilstein 'Online! Beilstein Institut zur Foerderung der Chemischen Wissenschaften, Frankfurt am Main, DE Database accession No. 282014, XP002206286.

*Primary Examiner*—Paul A. Zucker
(74) *Attorney, Agent, or Firm*—Oblon, Spivak, McClelland, Maier & Neustadt, P.C.

(57) ABSTRACT

Glyceric acid compounds of the formula (I)

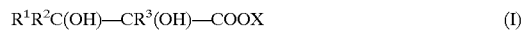

where $R^1$, $R^2$ and $R^3$ are independently hydrogen, $C_{1-12}$-alkyl, $C_{6-12}$-aryl, $C_{7-13}$-alkaryl or $C_{7-13}$-aralkyl and
X is hydrogen, an alkali metal, an alkaline earth metal/2 or $NH_4$,
are prepared by saponification of glycidic acid compounds of the formula (II)

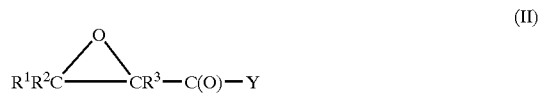

where Y is $NH_2$ or $OR^4$ in which $R^4$ is $C_{1-12}$-alkyl or $C_{7-13}$-aralkyl,
with ring-opening addition of water onto the epoxide ring.

Preferably, Y is $NH_2$ and the glycidamide of the formula (II) which is used is prepared by reacting acrylonitriles of the formula (III)

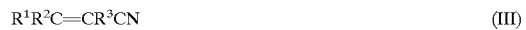

with hydrogen peroxide.

8 Claims, No Drawings

METHOD FOR THE PRODUCTION OF GLYCERIC ACID

The present invention relates to a process for preparing substituted or unsubstituted glyceric acid.

Glyceric acid is a chemical building block which is of interest for chemical syntheses and an intermediate for physiologically active compounds and amino acids.

Various methods of preparing glyceric acid are known.

DE-A 42 28 487 describes the preparation of glyceric acid by oxidation of glycerol by oxygen in the presence of catalysts. In particular, a catalyst comprising 1% of Ce and 5% of Pt on activated carbon is used, see Example 13.

JP-A 60 226 842 relates to the preparation of glyceric acid by reaction of acrylic acid with hydrogen peroxide in the presence of a tungsten-containing catalyst.

U.S. Pat. No. 3,846,478 relates to the oxidation of olefinic compounds to form glycols. Here, glyceric acid can likewise be prepared by catalytic oxidation of acrylic acid. Furthermore, the oxidation of acrylamide to glyceramide is described in Example 14. The oxidation is carried out using an alkali metal hypochlorite or alkaline earth metal hypochlorite in the presence of osmium tetroxide.

Disadvantages of the various process variants are an unsatisfactorily low selectivity in the oxidation of glycerol and the great difficulty of separating the secondary components from the desired product. Initially, the separation of homogeneous catalysts from the target product is problematical in the oxidation of acrylic acid.

It is an object of the present invention to provide a process for preparing substituted or unsubstituted glyceric acid which leads in high selectivity to substituted or unsubstituted glyceric acid, allows secondary components to be separated off simply and makes it possible to dispense with a catalyst.

We have found that this object is achieved by a process for preparing glyceric acid compounds of the formula (I)

$R^1R^2C(OH)-CR^3(OH)-COOX$        (I)

where $R^1$, $R^2$ and $R^3$ are independently hydrogen, $C_{1-12}$-alkyl, $C_{6-12}$-aryl, $C_{7-13}$-alkaryl or $C_{7-13}$-aralkyl and
X is hydrogen, an alkali metal, an alkaline earth metal/2 or $NH_4$,
by saponification of glycidic acid compounds of the formula (II)

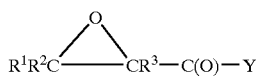

where Y is $NH_2$ or $OR^4$ in which $R^4$ is $C_{1-12}$-alkyl or $C_{7-13}$-aralkyl,
with ring-opening addition of water onto the epoxide ring.

"An alkaline earth metal/2" means that the alkaline earth metal ions are present in accordance with their stoichiometry, so that X is one equivalent of an alkaline earth metal ion.

According to the present invention, it has been found that glycidamides or glycidic esters can be converted in high yields and selectivities into the desired substituted or unsubstituted glyceric acids by saponification with ring-opening addition of water onto the epoxide ring.

In the formulae (I) and (II), $R^1$, $R^2$ and $R^3$ are preferably independently hydrogen, $C_{1-6}$-alkyl, phenyl, $C_{7-10}$-alkylphenyl or $C_{7-10}$-phenylalkyl. $R^1$, $R^2$ and $R^3$ are particularly preferably independently hydrogen or $C_{1-6}$-alkyl, in particular hydrogen or $C_{1-3}$-alkyl. $R^1$, $R^2$ and $R^3$ are particularly preferably hydrogen, so that the compound of the formula (I) is glyceric acid or a salt thereof and the compound of the formula (II) is glycidamide or a glycidic ester. In the glycidic esters of the formula (II), $R^4$ is preferably $C_{1-6}$-alkyl or $C_{7-10}$-phenylalkyl, particularly preferably $C_{1-3}$-alkyl. The glycidic acid compound of the formula (II) which is used is particularly preferably the amide. In particular, $R^1$, $R^2$ and $R^3$ are hydrogen and Y is $NH_2$, so that the glycidic acid compound of the formula (II) is glycidamide.

The preparation of glycidamide and glycidic esters is known per se. Appropriate processes are described, for example, in DE-A 19 04 077, DE-A 37 12 330 and DE-A 38 29 829.

Preferably, Y is $NH_2$ and the glycidamide of the formula (II) which is used is prepared by reacting acrylonitriles of the formula (III)

$R^1R^2C=CR^3CN$        (III)

with hydrogen peroxide. The preparation of glycidonitrile by reaction of acrylonitrile with hydrogen peroxide is known per se and is described, for example, in DE-A 19 04 077 and DE-A 38 29 829. For appropriate methods of preparation, reference may be made to these documents. Possible uses of glycidamide mentioned in these documents are the production of textile assistants, crop protection agents, preservatives and the production of dyes or the preparation of complexing agents such as isoserine-N,N-diacetic acid, but not the preparation of glyceric acid. DE-A 37 12 330, too, describes the use of glycidamide for the preparation of complexing agents.

Combining the reaction of acrylonitriles with hydrogen peroxide to form glyceramides and subsequent saponification with ring-opening addition of water onto the epoxide ring leads, in an uncomplicated overall process, to the desired substituted or unsubstituted glyceric acid in high yields and selectivities, with starting materials which remain in the reaction mixture or by-products being able to be separated off in a simple manner. In addition, it is possible to dispense with the use of catalysts as are described in the prior art.

The saponification is preferably catalyzed by acids or bases.

After reaction of the acrylonitriles of the formula (III), unreacted acrylonitriles of the formula (III) and other by-products can be separated from the reaction mixture by distillation.

After the reaction of the acrylonitriles of the formula (III) with hydrogen peroxide, unreacted hydrogen peroxide can also be decomposed.

In addition, when $Y=NH_2$, the ammonia formed in the saponification can be distilled off.

Glyceric acid salts of the formula (I) formed after a base-catalyzed saponification can be converted into free glyceric acids.

Taking glyceric acid as an example, the overall process can be summarized as follows:

a) reaction of acrylonitriles with aqueous hydrogen peroxide to form glycidamide, b) if appropriate, removal of unreacted acrylonitrile and other by-products from step a) by distillation, c) if necessary, decomposition of the unreacted hydrogen peroxide from step a), d) saponification of the glycidamide obtained to form an alkali metal salt or alkaline earth metal salt of glyceric acid or to form glyceric acid, e) if appropriate, removal of the ammonia formed by distillation,
f) if desired, conversion of the alkali metal salts or alkaline earth metal salts of glyceric acid into (free) glyceric acid.

The process of the present invention can be carried out continuously or batchwise. The process steps (a) and (d) are preferably carried out in a cascade of stirred vessels. However, other embodiments are also possible. Thus, some or all of the stirred vessels can be replaced by tube reactors.

The individual steps (a) to (f) will be described in more detail below for preferred embodiments using unsubstituted glyceric acid as an example:

(a) Acrylonitrile and an aqueous hydrogen peroxide solution having a strength in the range from 3 to 50% by weight, preferably from 10 to 25% by weight, are reacted with one another in a molar ratio of from 1:0.6 to 1:1.5, preferably from 1:1 to 1:1.2, at a pH of from 7 to 8, preferably from 7.3 to 7.7, and a temperature of from 30° C. to 60° C., preferably from 45° C. to 55° C., in a stirred vessel. The mean residence time in the stirred vessel is usually from 30 to 60 minutes.

To keep the pH and the temperature constant, 5–50% strength by weight, preferably 10–20% strength by weight, aqueous sodium hydroxide is metered in. The reaction solution is mixed further in from 1 to 3, preferably 1, downstream stirred vessel(s) under identical or similar pH and temperature conditions. The mean residence time in the second stirred vessel is usually from 15 to 90 minutes, preferably from 15 to 45 minutes.

(b) The acrylonitrile not reacted in (a), which is normally from 5 to 50% by weight, preferably from 10 to 30% by weight, of the amount used, and possible secondary components in step (a) which have boiling points lower than that of glycidamide are separated off in a distillation column which preferably operates according to the thin film evaporation principle. The distillation column is preferably operated at the same temperature as that in step (a) and at a pressure of advantageously from 50 to 160 mbar. Water is also present in the distillate.

The residual acrylonitrile of the reaction solution after the distillation is from 0.1 to 4% by weight. The acrylonitrile which has been separated off can, if desired, be returned to step (a) after removal of further substances.

(c) Step (c) is optional. Depending on how the saponification of the glycidamide is carried out, the decomposition of excess hydrogen peroxide before the saponification of the glycidamide may or may not be necessary. To decompose hydrogen peroxide still present, the reaction solution is passed over a solid catalyst, preferably activated carbon. However, it is also possible to use other solid materials for destroying the hydrogen peroxide, for example zeolites or water-insoluble manganese, lead, vanadium or noble metal compounds. The order of steps (b) and (c) can be exchanged.

(d) The saponification of the glycidamide can be either acid- or base-catalyzed. In the case of acid-catalyzed saponification, the glycidamide is reacted in the presence of water with an at least equimolar amount of an acid, for example sulfuric acid or phosphoric acid. The resulting ammonium salt of the respective acid can then be separated from the glyceric acid solution. However, the aqueous glycidamide solution is preferably passed over a heterogenous strong acid ion exchanger. An acid-catalyzed saponification forms glyceric acid as first product. For this reason, the acid-catalyzed saponification is preferred when glyceric acid is to be prepared directly.

However, should the salts of glyceric acid be the target compounds, the glyceric acid formed can simply be reacted with the corresponding metal oxides or hydroxides to give the glyceric acid salts.

In the case of base-catalyzed saponification, the glycidamide solution is reacted with a 10–50% strength by weight, preferably 40–50% strength by weight, solution of a basic alkali metal or alkaline earth metal compound, e.g. sodium hydroxide, potassium hydroxide or calcium hydroxide, in a molar ratio of from 1:1 to 1:1.7, preferably from 1:1.3 to 1:1.4, at a temperature of from 60 to 100° C., preferably from 70 to 95° C., and a pH of from 9 to 14, preferably from 11 to 12.5, in a stirred vessel to give the end product. The major part of the ammonia formed in the saponification can be removed from the product during the saponification by application of a reduced pressure of from 200 to 700 mbar or by stripping with nitrogen or another inert gas.

A thermal treatment of the aqueous glycidamide solution obtained from step (c) at temperatures of from 50 to 100° C. for from 10 minutes to 3 hours can optionally be carried out at the beginning of step (d) prior to the actual saponification reaction. The concentration of the glycidamide solution obtained from step (c) can optionally be changed by concentrating the solution or diluting the solution with, for example, water. Furthermore, acidic or basic, homogeneous or heterogeneous catalysts can optionally be added.

A specific embodiment of the process provides for the glycidamide solution to be treated in the presence of a catalyst with or without $CO_2$ prior to the saponification. Such catalysts can be, for example, metal halides, tetralkylammonium or tetralkylphosphonium halides and also metal oxides, metal hydrogen carbonates, metal carbonates, metal hydroxides and metalates such as molybdate, vanadate, tungstate. The treatment of the glycidamide solution with $CO_2$ is carried out at temperatures of preferably from 50° C. to 180° C. and pressures of preferably from 1 bar to 30 bar. The glycidamide solution which has been treated this way is subsequently saponified.

(e) The residual amount of the ammonia formed in the case of a basic saponification in (d) is separated off as a mixture with water in a stripping column or distillation column which preferably operates according to the thin film evaporator principle. The distillation column is preferably operated at the same temperature as that in step (d) and at a pressure of from 200 to 700 mbar, preferably from 400 to 600 mbar. This generally leaves a 2–20% strength by weight solution of the glyceric acid salt, which can be concentrated by distilling off water.

(f) If the base-catalyzed variant is chosen in step (d) and the target compound is glyceric acid, step (e) is followed by the conversion of the glyceric acid salt into glyceric acid.

The advantages of the process of the present invention are:

Selectivity to glycidamide in its preparation from acrylonitrile and hydrogen peroxide of >60%, based on the acrylonitrile reacted.

Simple removal of unreacted starting materials, and also, if necessary, removal of undesirable by-products.

The saponification of glycidamide to glyceric acid proceeds virtually quantitatively.

The invention is illustrated by the following examples:

EXAMPLES

Example 1

Preparation of Glycidamide from Acrylonitrile (a) 76.4 g/h (1.44 mol/h) of acrylontirile (AN) and 343 g/h of a 15% strength by weight aqueous hydrogen peroxide solution (corresponding to 1.51 mol of $H_2O_2$) together with 27 g/h of 8% strength by weight aqueous sodium hydroxide are metered at 50° C. into a stirred vessel R1 (volume: 0.3 l) so that the pH was maintained at from 7.4 to 7.5. After a residence time of 40 minutes, the reaction mixture was transferred to the stirred vessel R2 (volume: 0.5 l) where a further 29 g/h of 8% strength by weight aqueous sodium hydroxide were introduced to maintain the abovementioned pH. The temperature in the stirred vessel R2 was 50° C., and the residence time was 63 minutes.

(b) In a Sambay thin film evaporator D1, which was operated at 50° C. at 70 mbar, 90 g/h of distillate comprising unreacted acrylonitrile and water were distilled from the reaction mixture. 385 g/h of an aqueous glycidamide solution, which according to gas chromatography had a glycidamide content of about 60% by area, were obtained as bottoms.

Example 2

Ring-Opening Saponification of Glycidamide to Give Sodium Glycerate 250 g of a glycidamide solution from Example 1 are saponified with 613 g of 18.5% strength by weight aqueous sodium hydroxide at 100° C. and a pH of from 11.0 to 11.5 to give sodium glycerate.

We claim:

1. A process for preparing glyceric acid compounds of the formula (I)

$$R^1R^2C(OH)-CR^3-(OH)-COOX \qquad (I)$$

wherein $R^1$, $R^2$ and $R^3$ are independently hydrogen, $C_{1-12}$-alkyl, $C_{6-12}$-aryl, $C_{7-13}$-alkaryl or $C_{7-13}$-aralkyl and X is hydrogen, an alkali metal, an alkaline earth metal or $NH_4$, by saponification of glycidic acid compounds of the formula (II)

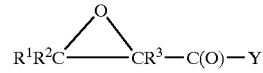  (II)

where Y is $NH_2$ with ring-opening addition of water onto the epoxide ring, wherein the glycidamide of the formula (II) which is used is prepared by reacting acrylonitriles of the formula (III)

$$R^1R^2C=CR^3CN \qquad (III)$$

with hydrogen peroxide.

2. A process as claimed in claim 1, wherein $R^1$, $R^2$ and $R^3$ are independently hydrogen or $C_{1-6}$-alkyl.

3. A process as claimed in claim 1, wherein $R^1$, $R^2$ and $R^3$ are hydrogen.

4. A process as claimed in claim 1, wherein the saponification is acid- or base-catalyzed.

5. A process as claimed in claim 1, wherein unreacted acrylonitriles of the formula (III) and other by-products are separated from the reaction mixture by distillation after the reaction of the acrylonitriles of the formula (III) with hydrogen peroxide.

6. A process as claimed in claim 1, wherein unreacted hydrogen peroxide is decomposed after the reaction of the acrylonitriles of the formula (III) with hydrogen peroxide.

7. A process as claimed in claim 1, wherein the ammonia formed in the saponification is distilled off.

8. A process as claimed in claim 1, wherein glyceric acid salts of the formula (I) formed in a base-catalyzed saponification are converted into free glyceric acids.

* * * * *